tes Patent (12) United States Patent
Althaus et al.

(10) Patent No.: US 11,635,148 B2
(45) Date of Patent: Apr. 25, 2023

(54) TUBE CLAMP

(71) Applicant: Horizon Healthcare LLC, Dayton, OH (US)

(72) Inventors: Joseph H. Althaus, Yellow Springs, OH (US); Ryan Muhlenkamp, Bellbrook, OH (US); Matthew B. Sunday, California, KY (US)

(73) Assignee: Horizon Healthcare LLC, Dayton, OH (US)

( * ) Notice: Subject to any disclaimer, the term of this patent is extended or adjusted under 35 U.S.C. 154(b) by 229 days.

(21) Appl. No.: 17/090,987

(22) Filed: Nov. 6, 2020

(65) Prior Publication Data

US 2021/0199204 A1    Jul. 1, 2021

Related U.S. Application Data

(60) Provisional application No. 62/954,172, filed on Dec. 27, 2019.

(51) Int. Cl.
*F16K 7/06*       (2006.01)
*F16L 3/10*       (2006.01)
(Continued)

(52) U.S. Cl.
CPC .............. *F16K 7/063* (2013.01); *F16L 3/10* (2013.01); *F16L 3/222* (2013.01); *F16L 55/10* (2013.01)

(58) Field of Classification Search
CPC ... F16K 7/063; F16K 7/04; F16K 7/06; F16K 7/065; F16K 7/066; F16K 3/22;
(Continued)

(56) References Cited

U.S. PATENT DOCUMENTS 2,595,511 A  *  5/1952 Butler ................. A61M 39/286
                                                     D23/245
3,915,167 A  * 10/1975 Waterman ........... A61M 39/284
                                                      251/9

(Continued)

FOREIGN PATENT DOCUMENTS

EP          2464406 B1    10/2016
WO     2014/144557 A2     9/2014
(Continued)

OTHER PUBLICATIONS

U.S. Appl. No. 17/090,996, filed Nov. 6, 2020, entitled "Tube Lock", Joseph H. Althaus et al.

*Primary Examiner* — Christopher Garft
(74) *Attorney, Agent, or Firm* — Thomas E. Lees, LLC (57) ABSTRACT

A tube holder includes a tube clamp having a housing and a clamping mechanism. The housing has a tube entry along a major surface thereof. A first tube passageway extends from the tube entry into the housing, and a tube receiving channel is coupled to the first tube passageway. The clamping mechanism comprises a lever handle user operable to transition from a first position to a second position. A gate is coupled to the lever handle, and a tube pinch is coupled to the lever handle. When a tube is peripherally inserted into the tube receiving channel and the lever handle of the clamping mechanism is in the second position, the gate prevents the tube from exiting the housing via the first tube passageway, and the tube pinch pinches the tube so as to prevent a flow of a fluid through the tube.

14 Claims, 9 Drawing Sheets

(51) Int. Cl.
*F16L 55/10* (2006.01)
*F16L 3/22* (2006.01)

(58) Field of Classification Search
CPC ..... F16L 55/10; F16L 55/1018; F16L 3/2235; F16L 3/10; F16L 3/1033; F16L 3/1041; F16L 3/075; F16L 3/22; F16L 3/221; A61M 5/1418; A61M 5/141
USPC .......................................... 248/49–74.5; 251/7
See application file for complete search history.

(56) References Cited

U.S. PATENT DOCUMENTS

| | | | |
|---|---|---|---|
| 5,423,769 A * | 6/1995 | Jonkman | A61M 39/284 604/250 |
| 5,910,135 A * | 6/1999 | Hadzic | A61M 39/286 604/251 |
| 6,368,315 B1 | 4/2002 | Gillis et al. | |
| 8,361,026 B2 | 1/2013 | Edwards et al. | |
| 8,398,617 B2 | 3/2013 | Ginggen et al. | |
| 8,524,259 B2 | 9/2013 | Taft et al. | |
| 8,882,830 B2 | 11/2014 | Cartledge et al. | |
| 9,079,758 B2 | 7/2015 | O'Dougherty et al. | |
| 9,358,378 B2 | 6/2016 | Hanson et al. | |
| 9,561,354 B2 | 2/2017 | Nebosky et al. | |
| 9,642,996 B2 | 5/2017 | Palmer et al. | |
| 9,743,877 B2 | 8/2017 | Pazart et al. | |
| 2003/0057390 A1* | 3/2003 | Blickhan | A61M 1/0236 604/6.1 |
| 2007/0135803 A1 | 6/2007 | Belson | |
| 2008/0290303 A1* | 11/2008 | Mackal | F16K 7/066 251/9 |
| 2009/0043253 A1 | 2/2009 | Podaima | |
| 2009/0118612 A1 | 5/2009 | Grunwald et al. | |
| 2012/0271237 A1* | 10/2012 | Andino | A61M 16/0003 604/174 |
| 2015/0174320 A1 | 6/2015 | Grant et al. | |
| 2016/0096003 A1 | 4/2016 | Parmar | |
| 2016/0281905 A1* | 9/2016 | Fox | F16L 59/135 |
| 2019/0167883 A1 | 6/2019 | Girouard et al. | |
| 2021/0199215 A1 | 7/2021 | Althaus et al. | |

FOREIGN PATENT DOCUMENTS

| | | |
|---|---|---|
| WO | 2014/165727 A1 | 10/2014 |
| WO | 2017/038575 A1 | 3/2017 |
| WO | 2017/087182 A1 | 5/2017 |
| WO | 2018/071651 A1 | 4/2018 |
| WO | 2019/118929 A1 | 6/2019 |

\* cited by examiner

TUBE CLAMP

CROSS REFERENCE TO RELATED APPLICATIONS

This application claims the benefit of U.S. Provisional Patent Application Ser. No. 62/954,172, filed Dec. 27, 2019, entitled "TUBE CLAMP", the disclosure of which is hereby incorporated by reference.

BACKGROUND

Various aspects of the present disclosure relate generally to clamps, and in particular, to clamps for tubes.

Tubes used for channeling fluid flow come in various sizes and are constructed of various materials. For instance, tubes such as catheters used for medical applications, are typically small diameter, hollow, flexible tubes. Catheters are typically constructed of a polymer, such as silicone rubber, nylon, polyurethane, polyethylene terephthalate (PET), latex, etc. Tubes also find application in automotive, industrial, robotics, commercial, consumer, and other applications, e.g., to carry fluid in mechanical systems.

BRIEF SUMMARY

According to aspects of the present disclosure, a tube holder comprises a tube clamp having a housing and a clamping mechanism. The housing has a tube entry along a major surface thereof. A first tube passageway extends from the tube entry into the housing, and a tube receiving channel is coupled to the first tube passageway. The clamping mechanism comprises a lever handle user operable to transition from a first position (e.g., an unclamped/unlocked position) to a second position (e.g., a clamped/locked position). A gate is coupled to the lever handle, and a tube pinch is coupled to the lever handle. Under this configuration, when a tube is peripherally inserted so as to pass from the tube entry through the first tube passageway and into the tube receiving channel, and the lever handle of the clamping mechanism is in the second position, the gate prevents the tube from exiting the housing via the first tube passageway, and the tube pinch pinches the tube so as to prevent a flow of a fluid through a pinch point of the tube.

According to further aspects of the present disclosure, a tube holder comprises a common housing and at least one tube clamp. Here, each tube clamp comprises a tube receiving channel that extends through the housing. Each tube clamp also comprises a clamping mechanism having a lever handle user operable to transition from a first position (e.g., an unclamped/unlocked position) to a second position (e.g., a clamped/locked position), and a tube pinch coupled to the lever handle. Under this configuration, when a tube is positioned within the tube receiving channel so as to pass through the housing, and the lever handle of the clamping mechanism is in the second position, the tube pinch pinches the tube so as to prevent a flow of a fluid through a pinch point of the tube.

According to yet further aspects of the present disclosure, a tube holder comprises a plurality of tube clamps positioned side by side. Each tube clamp has a housing having a tube entry along a major surface of the housing, a first tube passageway that extends from the tube entry into the housing, and a tube receiving channel coupled to the first tube passageway. Each tube clamp also has a clamping mechanism comprising a lever handle user operable to transition from a first position (e.g., an unclamped/unlocked position) to a second position (e.g., a clamped/locked position), a gate coupled to the lever handle, and a tube pinch coupled to the lever handle. Under this configuration, for a given tube clamp, when a tube is peripherally inserted so as to pass from the tube entry through the first tube passageway and into the tube receiving channel and the lever handle of the clamping mechanism is in the second position, the gate prevents the tube from exiting the housing via the first tube passageway, and the tube pinch pinches the tube so as to prevent a flow of a fluid through a pinch point of the tube. Here, each tube clamp can be implemented in a housing discrete from the tube clamps, or the housing for each tube clamp can define a common housing.

DETAILED DESCRIPTION

Tubes provide a convenient means to contain and enable the flow of fluids in an ordered and directed manner. In this regard, there are applications where is may be desirable to temporarily close off the flow of a fluid through a tube. This is often carried out using a valve. However, valves can be expensive, and have a number of parts, making the valve susceptible to wear and eventual failure. On the other hand, there are instances, e.g., using flexible tubing, where the tube material itself can act as a valve, such as by "pinching off" a hollow section defined by the inner diameter of the tube.

According to aspects of the present disclosure, a tube holder is disclosed that includes a tube clamp. The tube clamp is operated to selectively pinch a flexible tube held thereby, thus closing off a hollow section of the tube to prevent fluid from flowing through a pinch point of the tube. Certain embodiments include a tube holder for a single tube. Other embodiments facilitate holding any number of tubes in various configurations, e.g., parallel, in a common plane, etc. This can be accomplished by aggregating a set of independent tube clamps, or by including a set of tube clamps in a common housing. For instance, some embodiments provide for a customized or customizable number of tube clamps, e.g., by assembling various tube clamps (e.g., each tube clamp defining a clamp for one or more tubes), in various configurations. Other embodiments are pre-configured to a set number of tube clamps, e.g., one, two, three or more, etc., for a given housing.

Figure 1:
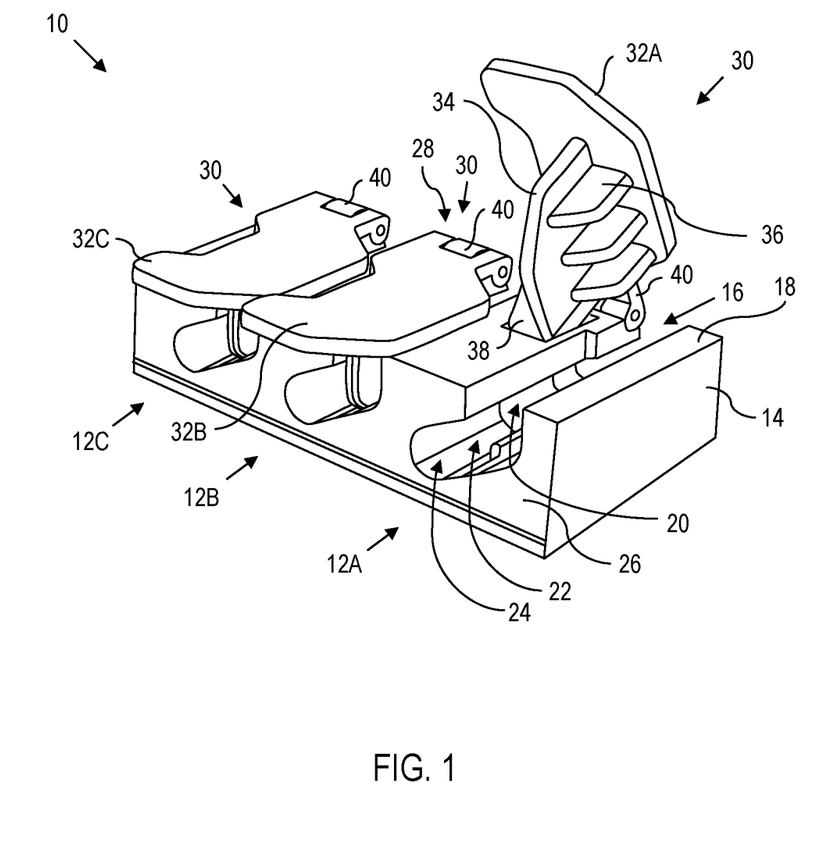
FIG. 1 is a perspective view of an example tube holder, according to aspects of the present disclosure herein.
Figure 2:
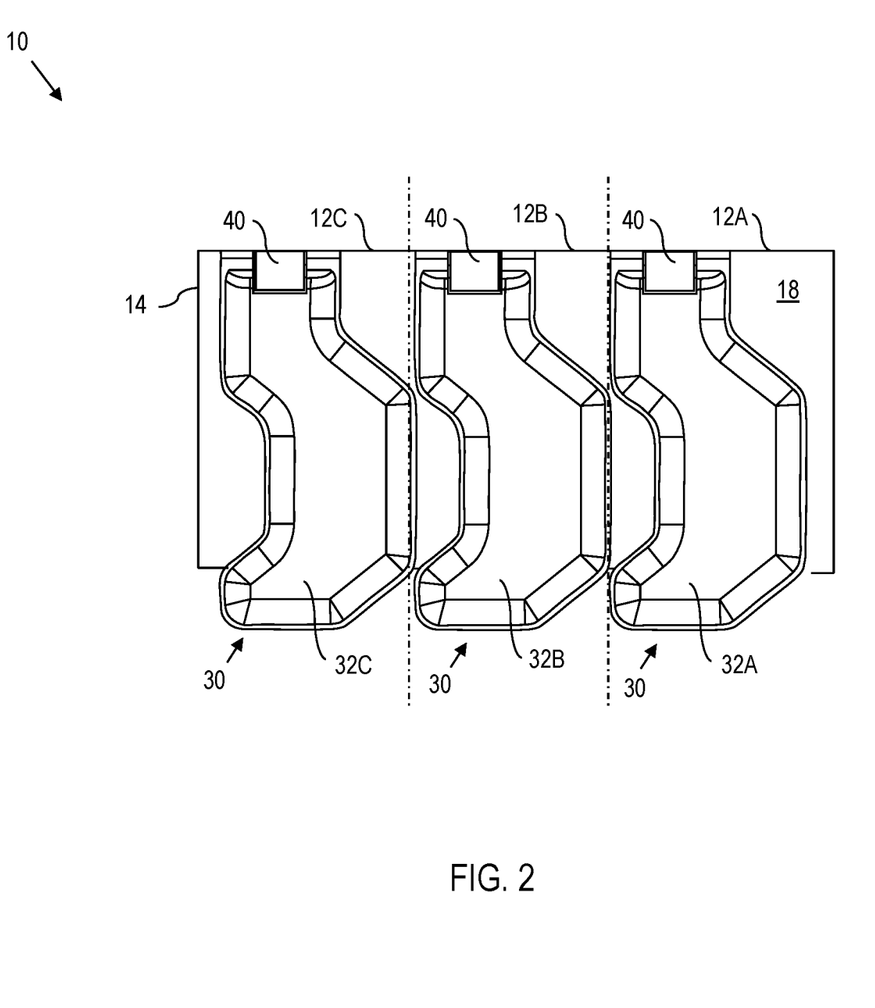
FIG. 2 is a top view of the tube holder of FIG. 1.

Referring to drawings and in particular to FIG. 1 and FIG. 2, a tube holder 10 is illustrated according to aspects of the present disclosure. The tube holder 10 includes at least one tube clamp 12. In the illustrated embodiment, three tube clamps 12 are illustrated solely for the convenience of illustration. As such, the tube clamps 12 are labeled tube clamp 12A for the rightmost position, tube clamp 12B for the middle position, and tube clamp 12C for the leftmost position. In practice, the tube holder 10 can include one tube clamp 12, or multiple (e.g., a set of) tube clamps 12. In this regard, tube clamp 12A, tube clamp 12B, and tube clamp 12C are identical, unless otherwise noted.

Each tube clamp 12 has a housing 14. In practice, each tube clamp 12 can have its own housing 14, e.g., tube clamp 12A can be contained in a housing 14 that is separable from the housing 14 of tube clamp 12B, etc. Alternatively, two or more tube clamps 12 can share a common housing 14. For instance, as illustrated, tube clamp 12A, tube clamp 12B, and tube clamp 12C are all contained in a common housing 14. In some embodiments, each tube clamp 12 is in a separate housing 14, and a tray or other structure is provided to snap, assemble, align, fasten, hold, or otherwise position multiple tube clamps 12 together.

Referring specifically to FIG. 1, in the illustrated embodiment, each tube clamp 12 has a housing 14 having a tube entry 16 along a major surface 18 of the housing 14. A first tube passageway 20 extends from the tube entry 16 into the housing 14. An optional second tube passageway 22 couples to the first tube passageway 20. Moreover, a tube receiving channel 24 is coupled to the first tube passageway 20. Notably, in some embodiments, the tube receiving channel 24 can couple/connect directly to the first tube passageway 20. In other embodiments, such as that shown in FIG. 1, the tube receiving channel 24 couples to the first tube passageway 20 via one or more connecting passageways, such as the second tube passageway 22, as shown.

Notably, in the illustrated embodiment, the tube entry 16 extends across the entire major surface 18 of the housing 14. Similarly, the first tube passageway 20 defines a first passthrough that slots through the housing 14 from a front face 26 through to a back face 28. In the illustrated embodiment, the front face 26 and back face 28 define surfaces that are adjacent to the major surface 18. In particular, the front face 26 and the back face 28 are each orthogonal to the major surface 18, and are generally parallel to each other. However, in other embodiments, the front face 26 and the back face 28 need not be parallel to each other.

Moreover, as illustrated, the first tube passageway 20 extends from the tube entry 16 into the housing 14 in a direction perpendicular to the major surface 18, e.g., straight down into the housing 14. However, in other embodiments, the first tube passageway 20 can extend into the housing at other angles. Moreover, the optional second tube passageway 22 connects the first tube passageway 20 to the tube receiving channel 24 such that the second tube passageway 22 extends angularly into the housing 14 from the first tube passageway 20 (and connecting to the tube receiving channel 24).

Moreover, in the example embodiment, the second tube passageway 22 defines a second passthrough that slots through the housing 14 from the front face 26 through to the back face 28. In this regard, the first tube passageway 20, the second tube passageway 22, and the tube receiving channel 24 form a "sock shape" profile on the front face 26 of the housing 14. By "slotting through" the housing, a tube can be peripherally inserted into the tube receiving channel 24. Peripheral insertion allows an axial length of the tube to be draped across the tube entry 16, and dropped down into the tube receiving channel 24. As such, there is no requirement that a tube tip/tube end is pushed through the housing 14. This can provide significant advantages, such as where a tube includes an adapter, head, port, or other device on an end thereof.

Notably, the tube entry 16, first tube passageway 20, second tube passageway 22, or combination thereof, enable peripheral insertion of a tube (e.g., inserting the tube into the tube holder by sliding a portion of the tube body/length into the tube holder 10 without axially pushing a tip of the tube through the housing 14). This approach makes the tube holder 10 compatible with applications that have/require fittings on the tube (e.g., some PICC-lines (Peripherally Inserted Central Catheter) or other medical tubes, some tubes with permanently installed connectors, etc.)

In alternative embodiments (e.g., where peripheral insertion is not a requirement because there are no fittings or other limitations on the tip of the tube), the housing 14 need not include the tube entry 16, first tube passageway 20, second tube passageway 22, or combination thereof. Rather, the tube receiving channel 24 can tunnel through the housing 14 via a hole/passageway that extends from the front face 26 through to the back face 28. This configuration allows a tube to be inserted into the tube housing 14 via a tip/end of the tube. The tube could then be slid along its length to a point where clamping is desired.

Referring generally to FIG. 1 and FIG. 2, each tube clamp 12 also includes a clamping mechanism 30. The clamping mechanism 30 includes a lever handle 32 that is user operable to transition from a first position (e.g., an unclamped/unlocked position) to a second position (e.g., a clamped/locked position). For instance, since there are three tube clamps 12A, 12B, 12C illustrated for sake of clarity, tube clamp 12A includes a lever handle 32A, tube clamp 12B includes a lever handle 32B, and tube clamp 12C includes a lever handle 32C. In FIG. 1, lever handle 32A is illustrated as being in the first position. Lever handle 32B and lever handle 32C are each illustrated in the second position. Comparatively, in FIG. 2, each lever handle 32 is in the second position.

Referring back to FIG. 1, and in particular, to the perspective view of the lever handle 32A, a gate 34 is coupled to the lever handle 32. In this regard, the gate 34 can include optional wings 36, which can provide reinforcement, etc. Additionally, a tube pinch 38 is coupled to the lever handle 32. Accordingly, when the lever handle 32 is in the second position (see for example lever handle 32B, and lever handle 32C), the gate 34 at least partially blocks the tube receiving channel 24 from the first tube passageway 20 (and in some embodiments, the gate 34 also at least partially blocks the tube receiving channel 24 from the second tube passageway 22). Yet further, in embodiments where there is no tube entry 16, first tube passageway 20, second tube passageway 22, etc., the gate 34 is not provided.

Regardless of whether or not a gate 34 is provided, when the lever handle 32 is in the second position (see for example lever handle 32B, and lever handle 32C), the tube pinch 38 is disposed in a "clamped position" relative to the tube receiving channel 24. The "clamped position" is a position that pinches a flexible tube installed/positioned within the tube receiving channel 24 by an amount that is sufficient to prevent the flow of fluid through the tube at the pinch point created by the tube pinch 38 cooperating with the tube receiving channel 24. In certain embodiments, this pinching/ clamping force also "locks" the tube to the tube clamp, e.g., such that the tube cannot readily be extracted from the tube receiving channel.

In some embodiments, the clamping mechanism 30 is further configured such that when the lever handle 32 is in the second position, the lever handle 32 at least partially covers the tube entry 16. This is most closely seen with regard to lever handle 32B and lever handle 32C.

As such, in some embodiments, when a tube is peripherally inserted so as to drop from the tube entry 16 through the first tube passageway 20 and into the tube receiving channel 24, and the lever handle 32 of the clamping mechanism 30 is in the second position (e.g., see lever handle 32B, and lever handle 32C), the gate 34 prevents the tube from exiting the housing 14 via the first tube passageway 20. Moreover, the tube pinch 38 pinches the tube so as to prevent a flow of a fluid through a pinch point of the tube.

To release a tube from the tube receiving channel 24, the lever handle 32 is moved to the first position, which allows the tube to peripherally lift out of the housing from the tube receiving channel 24 (or to pull through the tube receiving channel 24, e.g., where there is no fitting on the tube that would interfere).

For instance, in some embodiments, the clamping mechanism 30 is configured such that when the lever handle 32 is in the first position (e.g., see lever handle 32A), the gate 34 exposes the tube receiving channel 24 to the first tube passageway 20 and the tube pinch 38 is disposed in an unclamped position relative to the tube receiving channel 24. Thus, a corresponding tube dropped into the tube receiving channel 24 is not pinched, and thus fluid can flow through the tube. Also, the tube can be peripherally inserted or removed from the tube holder 10.

Referring again to FIG. 1 and FIG. 2, in some embodiments, the clamping mechanism 30 is hinged via hinge 40 so as to pivot about the first major surface 18 of the tube clamp 12. The hinge 40 allows ready transitioning of the clamping mechanism 30 between the first position to the second position (e.g., open and closed positions). In this regard, the hinge 40 can optionally include a spring or other feature to facilitate a tactile operation. An optional spring can also be used to bias the clamping mechanism 30 closed such that a tube positioned in the tube receiving channel 24 is pinched closed. In some embodiments, a "snap", "clasp", hook, click lock or other feature may be used (e.g., as part of the clamping mechanism 30 or otherwise) to ensure that when the clamping mechanism 30 is in the closed position, a tube positioned therein remains pinched closed. In this regard, the type of tube, tube flexibility, tube diameter, etc., may influence the manner in which the clamping mechanism remains closed.

In some embodiments, the tube clamp is configured to accept medical tubes. In this regard, a width of the tube entry 16 (FIG. 1) and tube receiving channel 24 are sufficient to enable insertion of the tube, where the tube is implemented as at least one of a central line catheter, an intravenous line, a PICC-line, a fluid carrying flexible tube, etc. By way of non-limiting example, a tube diameter can range from approximately 1-11 millimeters. In other applications, such as robotics, industrial, automotive, consumer, etc., the tube entry 16 (FIG. 1) was a sufficient width to accommodate the largest tube diameter that is anticipated to be used by the device.

As noted above, the clamping mechanism 30 includes a tube pinch 38 (FIG. 1) that pinches a tube peripherally inserted into the tube receiving channel 24 (FIG. 1). In this regard, in an embodiment that utilizes a hinge 40, operation of the lever handle 32 from the open to the closed position may correspondingly pivot the tube pinch 38 from a "pinch" position with the tube receiving channel to a spaced position, which may require the tube pinch 38 to travel through the housing 14.

Figure 3:
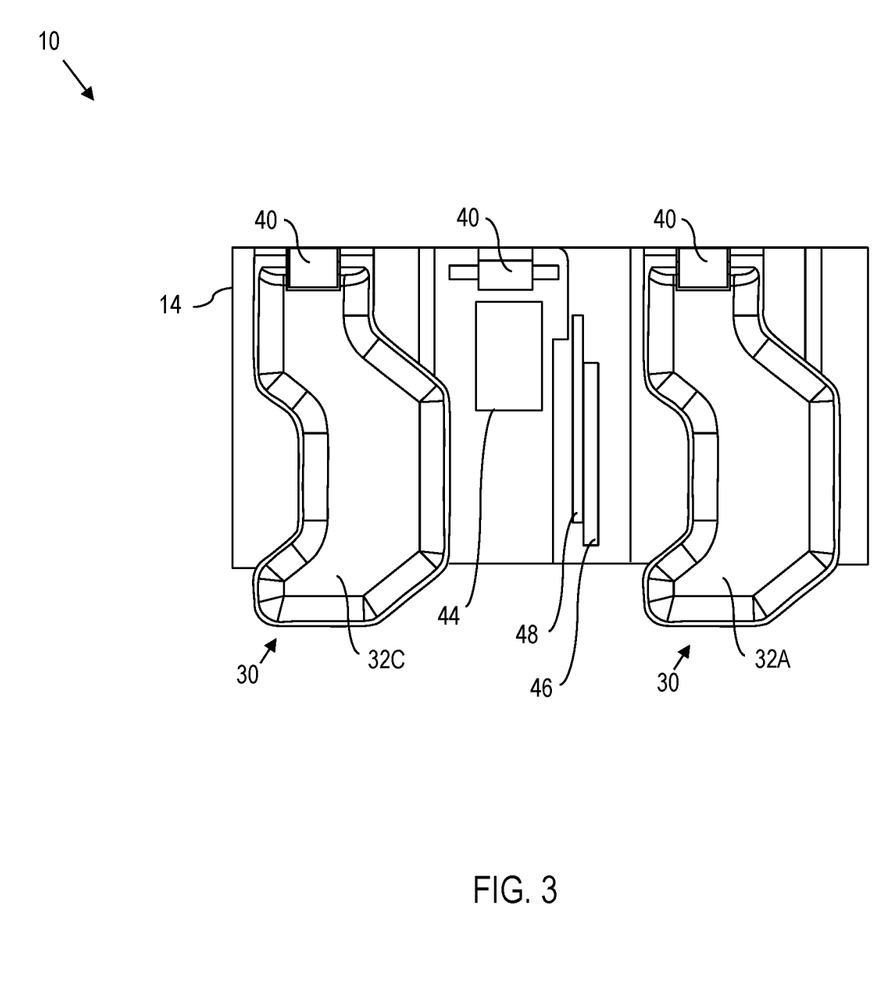
FIG. 3 is a top view of the tube holder of FIG. 1, having a lever handle removed to illustrate features of the housing, according to aspects of the present disclosure.
Figure 4:
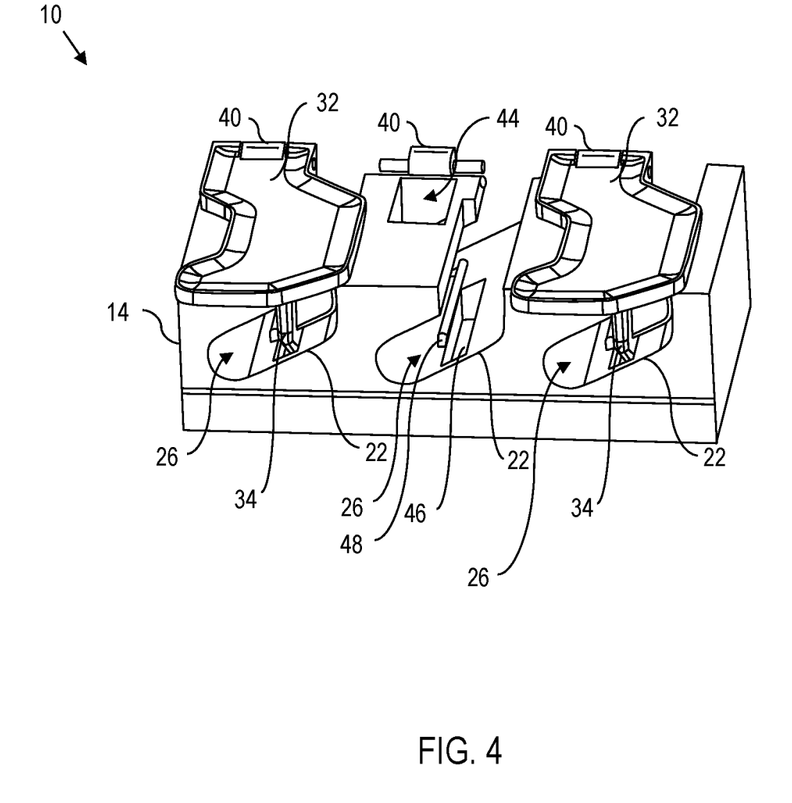
FIG. 4 is a perspective view of the tube holder of FIG. 1, having a lever handle removed to illustrate features of the housing, according to aspects of the present disclosure.
Figure 5:
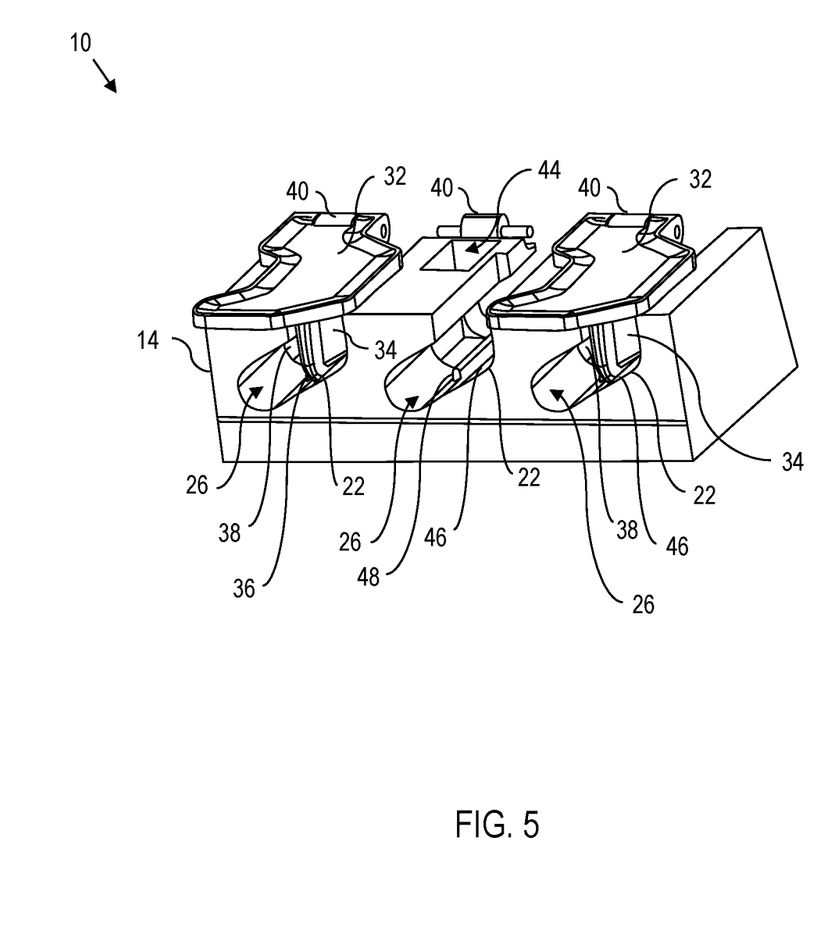
FIG. 5 is another perspective view of the tube holder of FIG. 1, having a lever handle removed to illustrate features of the housing, according to aspects of the present disclosure.

Referring to FIG. 3, FIG. 4, and FIG. 5 generally, the tube holder 10 is illustrated with the lever handle 32B (FIG. 1 and FIG. 2) removed for clarity of illustration. In this regard, FIG. 3-FIG. 5 illustrate various features of the tube holder 10 that are common, including features common with FIG. 1 and/or FIG. 2. As such, like structure is illustrated with like reference numbers and a detailed description is omitted except to clarify differences.

Notably, an aperture 44 extends through the first major surface 18 and forms a pinch passageway into the housing 14. The aperture 44 and corresponding pinch passageway allows the tube pinch 38 to transition into and out of the tube receiving channel 24 as the lever handle 32 is pivoted about the hinge 40 between open and closed positions.

In some embodiments, the housing 14 can also include a gate receiving channel 46. The gate receiving channel 46 is positioned in the second tube passageway 22 in the illustrated embodiment. However, in practice, the gate receiving channel 46, where provided, can be positioned anywhere in the housing 14 that aligns in register with the gate 34 of the clamping mechanism 30. Notably, when the handle lever 32 is in the closed position, and when a tube has been peripherally inserted into the tube receiving channel 24, at least an edge of the gate 34 sits into the gate receiving channel 46. Because the gate receiving channel 46 recesses into the housing 14 from the second tube passageway 22, the tube is physically blocked from exiting the tube holder 10. In some embodiments, the tube cannot be withdrawn from the tube receiving channel back through the second tube passageway 22 because the gate 34 cooperates with the gate receiving channel 46 to physically block the entire second tube passageway 22.

The gate 34 can also be used to ensure proper loading of the device. For instance, if a tube were to be positioned over the tube entry 16, and the lever handle 32 is transitioned from the open to the closed position, the edge of the gate 34 would push the tube peripherally down the first tube passageway 20, through the second tube passageway 22, and into the tube receiving channel 24. The gate 34 would disengage the tube as the edge of the gate 34 enters the gate receiving channel 46.

Also as illustrated, in some embodiments, each tube clamp 12 can include a barricade 48 forming a divider between the second tube passageway 22 and the tube receiving channel 24. The barricade 48 prevents a tube peripherally inserted into the tube receiving channel 24 from slipping out, e.g., during handling and until the lever handle is transitioned to the second position (closed position).

Figure 6:
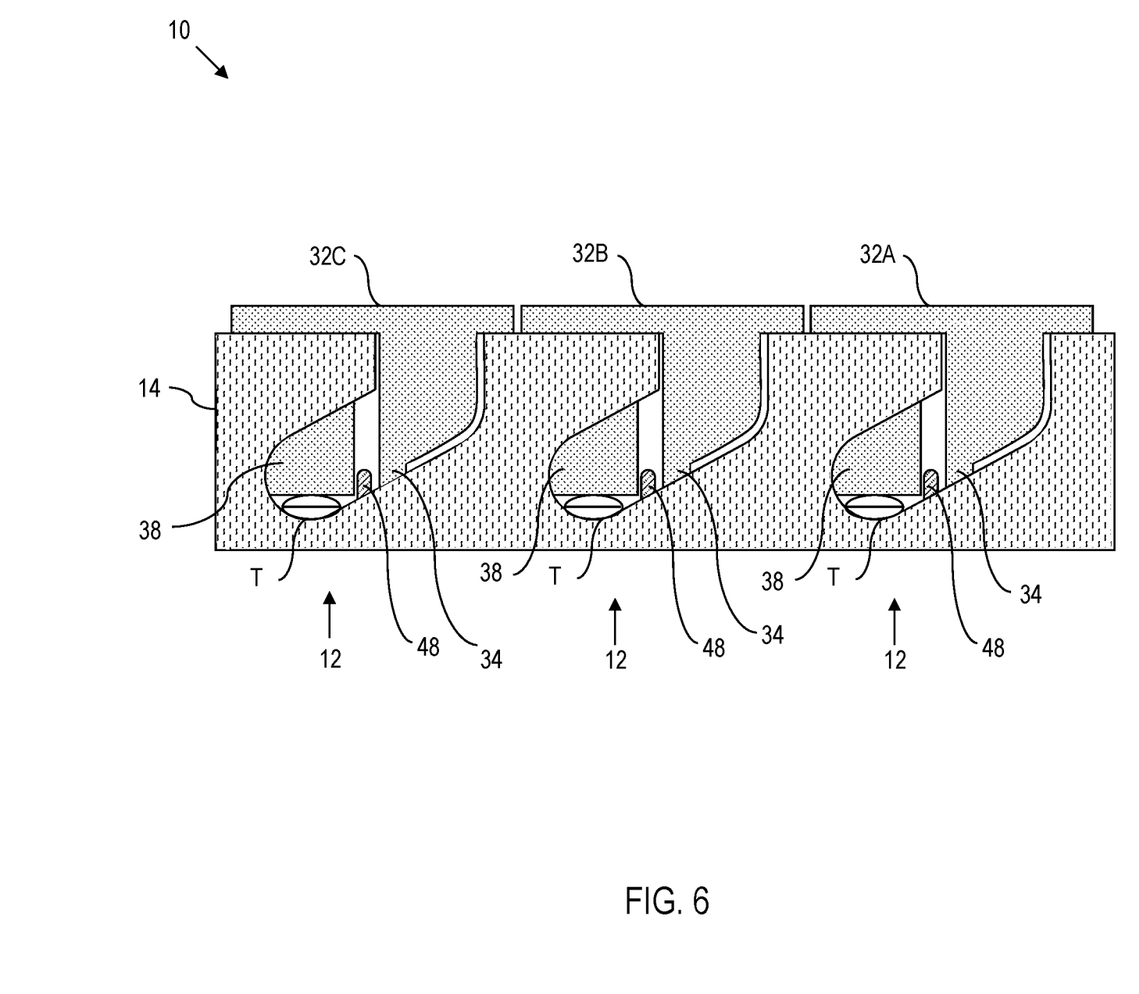
FIG. 6 is a front side view of a simplified tube holder, according to aspects of the present disclosure herein.
Figure 7:
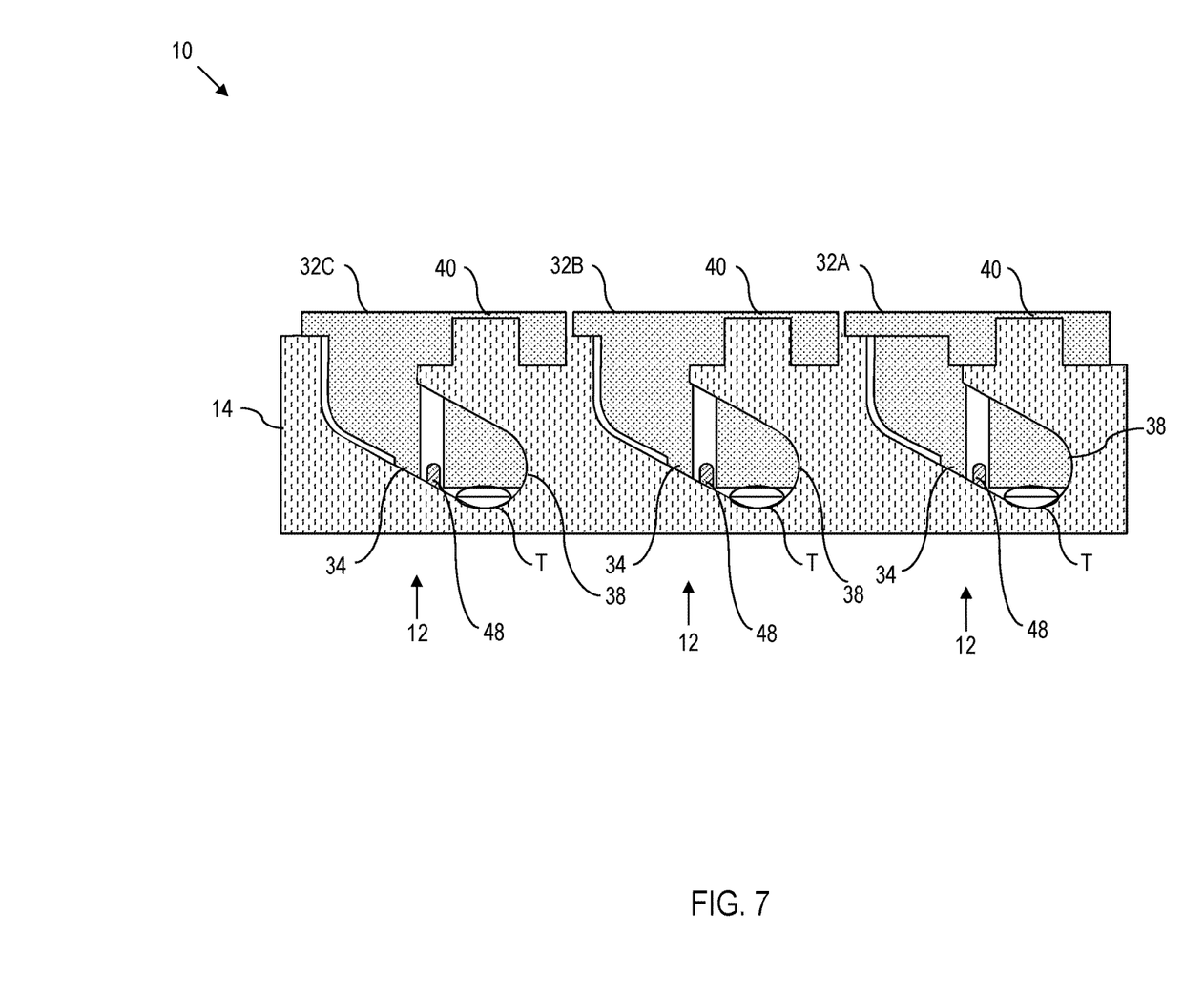
FIG. 7 is a back side view of the simplified tube holder of FIG. 6, according to aspects of the present disclosure herein.

Referring to FIG. 6 and FIG. 7, a front an back view respectively, of a tube holder 10 is illustrated in simplified schematic form. The tube holder 10 is identical to the tube holder described herein with regard to FIG. 1-FIG. 5, but with certain features omitted or illustrated in simplified schematic form for clarity of discussion. Notably, the handle lever 32A, the handle lever 32B, and the handle lever 32C are each hinged via hinge 40 to the second (closed) position. Since each tube clamp 12 is independent, the illustrated state is purely arbitrary and each tube clamp 12 can be in an open or closed state.

Notably, as illustrated, when the lever handle 32A is in the closed position, the gate 34 closes off the second tube passageway 22 from the tube receiving channel 24. The gate 34 cooperates with the barricade 48, thus preventing a tube "T" peripherally inserted into the tube receiving channel 24 from exiting the tube holder 10.

Also as illustrated, the tube pinch 38 compresses the volume within the tube receiving channel 24 sufficient to deform the flexible tube T, thus pinching the tube and preventing fluid flow through the pinch point.

Figure 8:
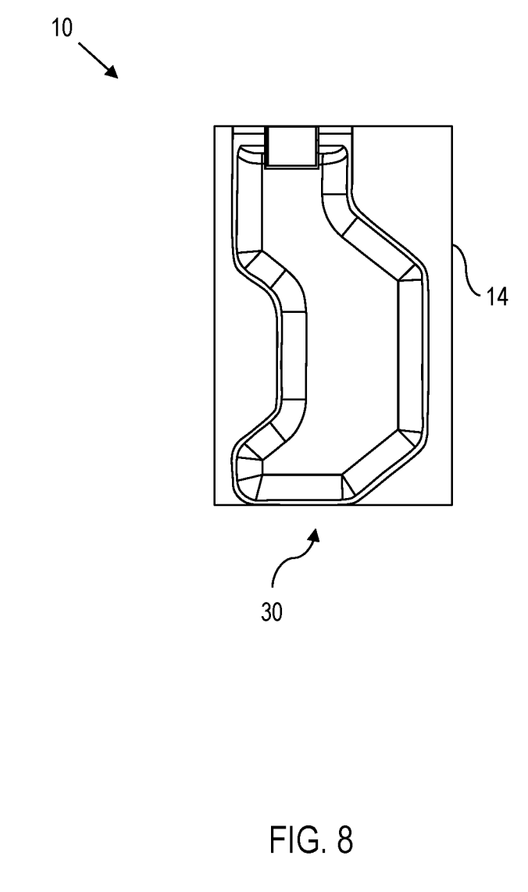
FIG. 8 illustrates a single tube clamp.
Figure 9:
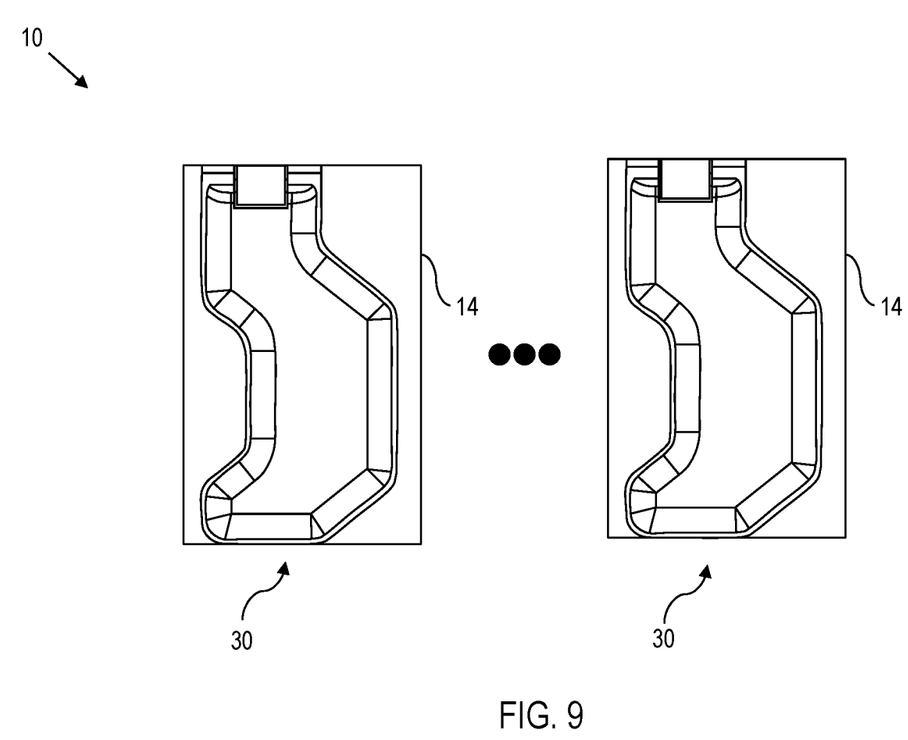
FIG. 9 illustrates an arbitrary number of independent tube clamps positioned adjacent to one another.

Referring generally to FIG. 8 and FIG. 9, embodiments are illustrated where a tube holder 10 includes a single tube clamp (FIG. 8), or an arbitrary number of tube clamps (FIG. 9). Notably, FIG. 9 illustrates a first tube clamp, and at least one additional tube clamp, the at least one additional tube clamp being identical in function to the first tube clamp and positioned laterally adjacent to the first tube clamp. Here, the tube clamps can be provided in a common housing, or each tube clamp can be in a separate housing that are situated adjacent to each other. In the later example, a carrier, holder, carton or other structure can be used to keep the tube clamps together.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. Aspects of the disclosure were chosen and described in order to best explain the principles of the disclosure and the practical application, and to enable others of ordinary skill in the art to understand the disclosure for various embodiments with various modifications as are suited to the particular use contemplated.

What is claimed is:

1. A tube holder comprising:
   a tube clamp having:
      a housing having a tube entry along a major surface thereof, wherein the tube entry extends across the entire major surface of the housing;
      a first tube passageway that extends from the tube entry into the housing;
      a tube receiving channel coupled to the first tube passageway; and
      a second tube passageway that connects the first tube passageway to the tube receiving channel, wherein the second tube passageway extends angularly into the housing from the first tube passageway;
      a barricade forming a divider between the second tube passageway and the tube receiving channel;
      a clamping mechanism, the clamping mechanism having:
         a lever handle user operable to transition from a first position to a second position;
         a gate coupled to the lever handle; and
         a tube pinch coupled to the lever handle;
      wherein:
         when a tube is peripherally inserted so as to pass from the tube entry through the first tube passageway and into the tube receiving channel and the lever handle of the clamping mechanism is in the second position:
            the gate prevents the tube from exiting the housing via the first tube passageway; and
            the tube pinch pinches the tube so as to prevent a flow of a fluid through a pinch point of the tube; and
         the first tube passageway defines a first passthrough that slots through the housing from a front face through to a back face, where the front face and back face define surfaces that are adjacent to the major surface.

2. The tube holder of claim 1, wherein:
   the clamping mechanism is configured such that:
      when the lever handle is in the first position, the gate exposes the tube receiving channel to the first tube passageway and the tube pinch is disposed in an unclamped position relative to the tube receiving channel; and
      when the lever handle is in the second position, the gate at least partially blocks the tube receiving channel from the first tube passageway, and the tube pinch is disposed in a clamped position relative to the tube receiving channel.

3. The tube holder of claim 1, wherein:
   The clamping mechanism is further configured such that when the lever handle is in the second position, the lever handle at least partially covers the tube entry.

4. The tube holder of claim 1, wherein the first tube passageway extends from the tube entry into the housing in a direction perpendicular to the major surface.

5. The tube holder of claim 1, wherein:
   the second tube passageway defines a second passthrough that slots through the housing from the front face through to the back face.

6. The tube holder of claim 1, wherein:
   the clamping mechanism is hinged so as to pivot about the first major surface of the clamp.

7. The tube holder of claim 1, wherein a width of the tube entry is sufficient to enable insertion of the tube, where the tube is implemented as at least one of:
   a central line catheter;
   an intravenous line;
   a PICC-line; and
   a fluid carrying flexible tube.

8. The tube holder of claim 1 further comprising:
   an aperture extending through the first major surface and into the housing that allows the tube pinch to transition into and out of the tube receiving channel.

9. The tube holder of claim 1, wherein:
   the tube clamp comprises a first tube clamp;
   further comprising:
   at least one additional tube clamp, the at least one additional tube clamp being identical in function to the first tube clamp and positioned laterally adjacent to the first tube clamp in a common housing.

10. A tube holder comprising:
    a common housing; and
    at least one tube clamp, each tube clamp having:
       a tube entry along a major surface of the common housing;

a tube receiving channel that extends through the housing;

a first tube passageway that extends from the tube entry into the common housing, such that the tube receiving channel is coupled to the first tube passageway; and a clamping mechanism, the clamping mechanism having:

a lever handle user operable to transition from a first position to a second position;

a gate coupled to the lever handle;

a tube pinch coupled to the lever handle;

the clamping mechanism is configured such that:

when the lever handle is in the first position, the gate exposes the tube receiving channel to the first tube passageway and the tube pinch is disposed in an unclamped position relative to the tube receiving channel; and when the lever handle is in the second position, the gate at least partially blocks the tube receiving channel from the first tube passageway, and the tube pinch is disposed in a clamped position relative to the tube receiving channel; and the clamping mechanism is further configured such that when the lever handle is in the second position, the lever handle at least partially covers the tube entry;

a second tube passageway that connects the first tube passageway to the tube receiving channel, wherein the second tube passageway extends angularly into the housing from the first tube passageway;

the second tube passageway defines a second passthrough that slots through the housing from the front face through to the back face; and a barricade forming a divider between the second tube passageway and the tube receiving channel, wherein:

when a tube is positioned within the tube receiving channel so as to pass through the housing and the lever handle of the clamping mechanism is in the second position:

the tube pinch pinches the tube so as to prevent a flow of a fluid through a pinch point of the tube.

11. The tube holder of claim 10, wherein:

the tube entry extends across the entire major surface of the housing;

the first tube passageway defines a first passthrough that slots through the housing from a front face through to a back face, where the front face and back face define surfaces that are adjacent to the major surface; and the first tube passageway extends from the tube entry into the housing in a direction perpendicular to the major surface.

12. The tube holder of claim 10, wherein:

the clamping mechanism is hinged so as to pivot about the first major surface of the clamp.

13. The tube holder of claim 10, wherein the tube receiving channel is sufficient to enable insertion of the tube, where the tube is implemented as at least one of:

a central line catheter;

an intravenous line;

a PICC-line; and a fluid carrying flexible tube.

14. The tube holder of claim 10 further comprising:

an aperture extending through the first major surface and into the housing that allows the tube pinch to transition into and out of the tube receiving channel.

\* \* \* \* \*